(12) United States Patent
Flach et al.

(10) Patent No.: US 8,126,545 B2
(45) Date of Patent: Feb. 28, 2012

(54) ACTIVE IMPLANTABLE MEDICAL DEVICE WITH AT LEAST TWO DIAGNOSTIC AND/OR THERAPEUTIC FUNCTIONS

(75) Inventors: Erhard Flach, Berlin (DE); Wolfgang Geistert, Rheinfelden (DE); Roland Jacobsen, Berlin (DE); Max Schaldach, Berlin (DE); Axel Ulbrich, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 801 days.

(21) Appl. No.: 11/738,277

(22) Filed: Apr. 20, 2007

(65) Prior Publication Data

US 2007/0250120 A1  Oct. 25, 2007

(30) Foreign Application Priority Data

Apr. 22, 2006 (DE) .......................... 10 2006 018 851

(51) Int. Cl.
*A61N 1/00* (2006.01)
(52) U.S. Cl. ................ 607/2; 607/36; 607/37; 600/300
(58) Field of Classification Search ................ 607/2, 36, 607/37, 38, 60; 600/300
See application file for complete search history.

(56) References Cited

U.S. PATENT DOCUMENTS

| 5,411,535 | A | * | 5/1995 | Fujii et al. ........................ 607/32 |
| 5,593,430 | A | * | 1/1997 | Renger ........................... 607/18 |
| 5,810,735 | A |   | 9/1998 | Halperin |
| 5,919,213 | A |   | 7/1999 | Nelson et al. |
| 5,999,848 | A | * | 12/1999 | Gord et al. ........................ 607/2 |
| 6,141,588 | A |   | 10/2000 | Cox et al. |
| 6,823,208 | B2 | * | 11/2004 | Ohlsson ........................ 600/509 |
| 2003/0020810 | A1 |   | 1/2003 | Takizawa et al. |
| 2003/0023150 | A1 |   | 1/2003 | Yokoi et al. |
| 2004/0176814 | A1 | * | 9/2004 | Singhal et al. .................. 607/45 |
| 2005/0055056 | A1 |   | 3/2005 | Olson |

FOREIGN PATENT DOCUMENTS

| DE | 3831809 | 3/1990 |
| DE | 102005007576 | 8/2006 |
| WO | WO 2005/061050 | 7/2005 |
| WO | WO 2006/077530 | 7/2006 |

OTHER PUBLICATIONS

German Search Report, dated Feb. 7, 2007.
European Search Report, dated Jul. 2, 2007.

* cited by examiner

*Primary Examiner* — Carl H Layno
*Assistant Examiner* — Pamela M Bays
(74) *Attorney, Agent, or Firm* — ARC IP Law, PC; Joseph J. Mayo

(57) ABSTRACT

An active medical implantable device with at least two diagnostic and/or therapeutic functions is constructed from separate active implant modules (2 to 7) which are adapted to the respective desired functions and can be coupled to each other.

6 Claims, 3 Drawing Sheets

ACTIVE IMPLANTABLE MEDICAL DEVICE WITH AT LEAST TWO DIAGNOSTIC AND/OR THERAPEUTIC FUNCTIONS

This application takes priority from German Patent Application DE 10 2006 018 851.9 filed 22 Apr. 2006, the specification of which is hereby incorporated herein by reference.

BACKGROUND OF THE INVENTION

1. Field of the Invention

The invention relates to an active implantable medical device with at least two diagnostic and/or therapeutic functions.

2. Description of the Related Art

A multiplicity of different types of active implants such as heart pacemakers, defibrillators, insulin pumps, neurostimulators, body function recording devices (so-called "event recorders"), heart support systems, etc. The common characteristic of these implants is that they are designed for a certain application and have a functionality determined by the device manufacture. The latter is generally directed towards a certain disease of the implant carrier that is to be diagnosed and/or treated by the implant.

However, many patients have not only a certain disease but also a plurality of or systemic symptoms which require a diagnosis or therapy. Moreover, systemic monitoring may often be all that is required. This is generally difficult to achieve with a predetermined implant because the individual components required for this are systemically associated with other and are subject to mutual influence.

Because of the problem outlined there is therefore a requirement for an implant which can be individually matched to complex symptoms or diagnosis requirement of a patient and can be configured so that, if necessary, different types of information can be received at a plurality of points on the body, processed and a suitable therapy in turn derived and applied on the basis of this information.

SUMMARY OF THE INVENTION

The object of this invention is therefore to provide an active, medical implantable device which can be suitably configured by the doctor during the implantation procedure to meet the individual requirements of the patient.

This object is achieved according to claim 1 in that separate active implant modules, which can be coupled to each other, are provided with at least two diagnostic and/or therapeutic functions for these modules.

On the basis of this modular system the individual modules can each be designed for a particular application, e.g. for measuring physical or chemical parameters and, based on this, for calculating physiological parameters for diagnosis purposes. Again on this basis a particular therapy can be applied by the active implantable device. The following may be mentioned as examples of such physical and chemical parameters:
body temperature
electrical values (voltage, current, impedance)
pressure
acceleration
optical values (colour, light permeability)
viscosity
pH value
time Physical parameters that can be determined from the above then include, for example:
cardiac frequency
respiratory frequency
nerve and brain activity
oxygen saturation
lactic acid concentration
cholesterol content
histamine content
movement (activity)

Therapies that can be derived from the above include, for example:
electrical stimulation (low and high energy), e.g. heart pacemaker or defribrillator)
mechanical stimulation
administration of medicines (e.g. insulin pump)

In principle it is possible, on the basis of this concept, to implement one or a plurality of the functionalities listed above in one module, and to provide modules with special tasks, for example the supply of current to the other modules and their intercommunication. In this connection it may be advantageous to provide a base device component whereby the implant modules can be coupled, thus enabling the entire system to be implemented in a compact, "elegant" fashion.

The base device component preferably receives multi-functional basic elements for the implantable devices, for example a central control unit, a communication unit and/or a power supply unit for the implant modules.

According to an advantageous embodiment a bus system is provided for coupling the modules and, in particular, their control and/or communication, which bus system is constructed, for example, of a plurality of electrical conductors or is designed on the basis of light conductor technology.

In this case the bus system may be designed so that the implant modules can, for the purpose of their coupling, be connected in terms of signal transmission and mechanically to the bus system, and preferably installed along it. Modules are therefore "docked" onto the bus system, for which purpose provision is made for the bus system to be guided through the individual modules and the implant modules installed along it, preferably by means of plug-in couplings.

However, the modules can also be coupled by means of a wireless bus system, which is particularly advantageous when the individual implant modules are not intended to form a compact, mechanical unit after coupling, but are to be installed distributed in the body. Such a wireless communication can be achieved, for example, with a radio technology such as "Blue Tooth", an inductive coupling or a galvanic coupling via a conductive body fluid.

According to a further preferred embodiment an implant module can be fitted with replaceable sub-modules. The latter preferably deviate from the actual functionality of the implant module so that the latter can be variably expanded in terms of its scope of functions. This addition, or even refitting, may also be carried out at later date after the initial installation of the implantable device, without having to replace the complete implant.

Summarising, the implantable device according to the invention allows very flexible adaptation to diagnostic and therapeutic requirements which, even after the initial installation of the implant, can still be achieved at limited expense and without having to replace the entire implant.

BRIEF DESCRIPTION OF THE DRAWINGS

Further features, advantages and details of the invention are evident from the following description of an exemplary embodiment with reference to the attached drawings, in which.

DETAILED DESCRIPTION OF THE INVENTION

Figure 1:
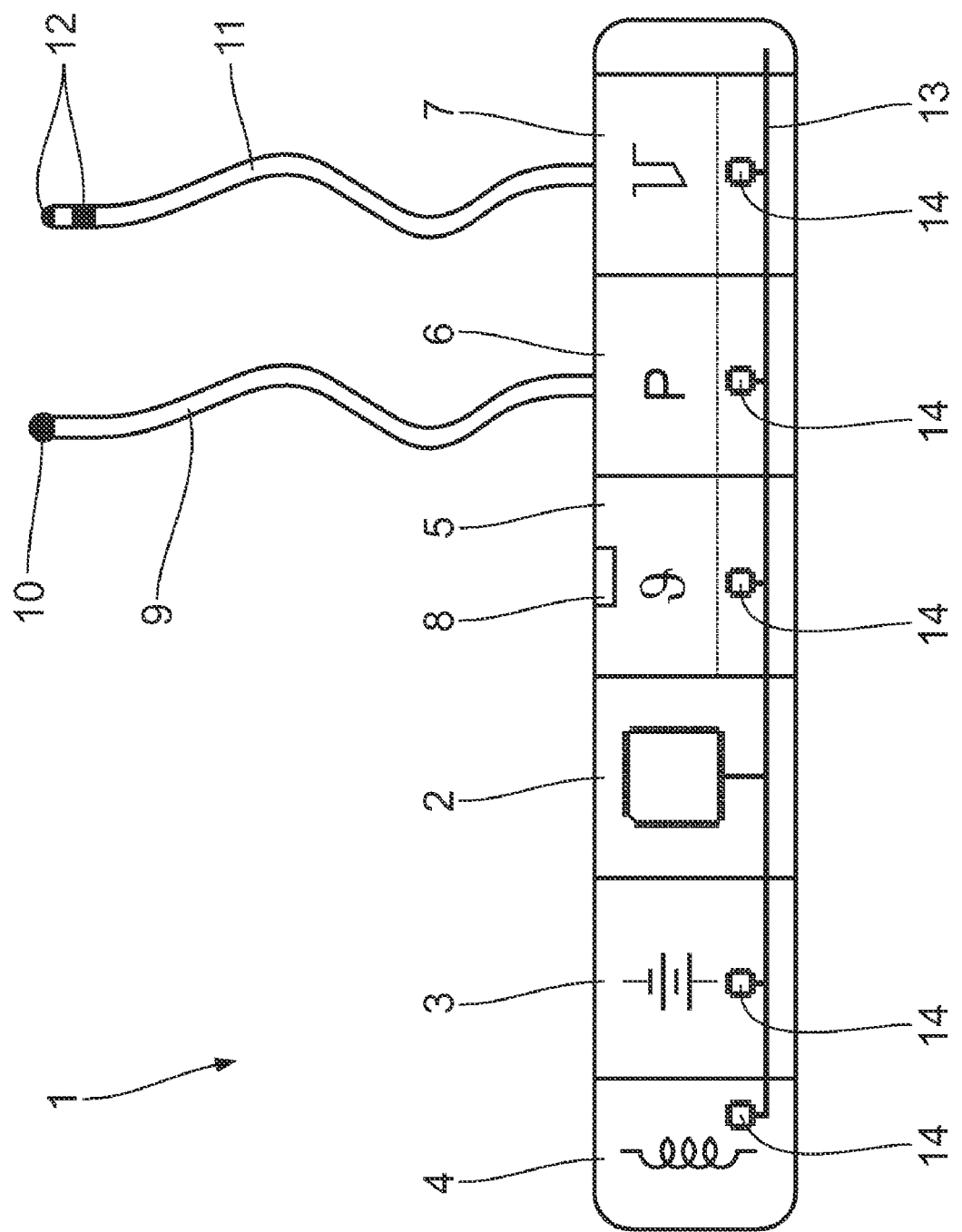
FIG. 1 shows a diagrammatic representation of an active medical implantable device in a modular design.

The basic concept of medical implantable device 1 can be explained with reference to FIG. 1. This has different modules, namely a central control module 2, a power supply module 3 and a communication module 4, which is constructed, for example, on the basis of a transponder and via which implantable device 1 is able to communicate with an external base device. Furthermore, implantable device 1 has two diagnostic measuring modules 5, 6 for measuring temperature and pressure, and a therapeutic module 7 for electrical stimulation. A temperature sensor 8 is integrated in measuring module 5, which serves to measure temperature. When the implantable device is installed in a patient body, this sensor records the body temperature.

Measuring module 6 serves to determine pressure P in a body part and for this purpose has a measuring cable 9 running from measuring module 6, at the free end of which cable is fitted a pressure sensor 10.

Therapeutic module 7 has a connected catheter 11 at the free end of which lie stimulation electrodes 12. The patient body may therefore be electrically stimulated, i.e. a heart pacemaker function may be provided, for example.

Modules 2 to 7 are commonly connected together by a bus system 13, which is coupled via interfaces 14 to each module 3 to 7 for the purpose of signal transmission and power supply.

Figure 2:
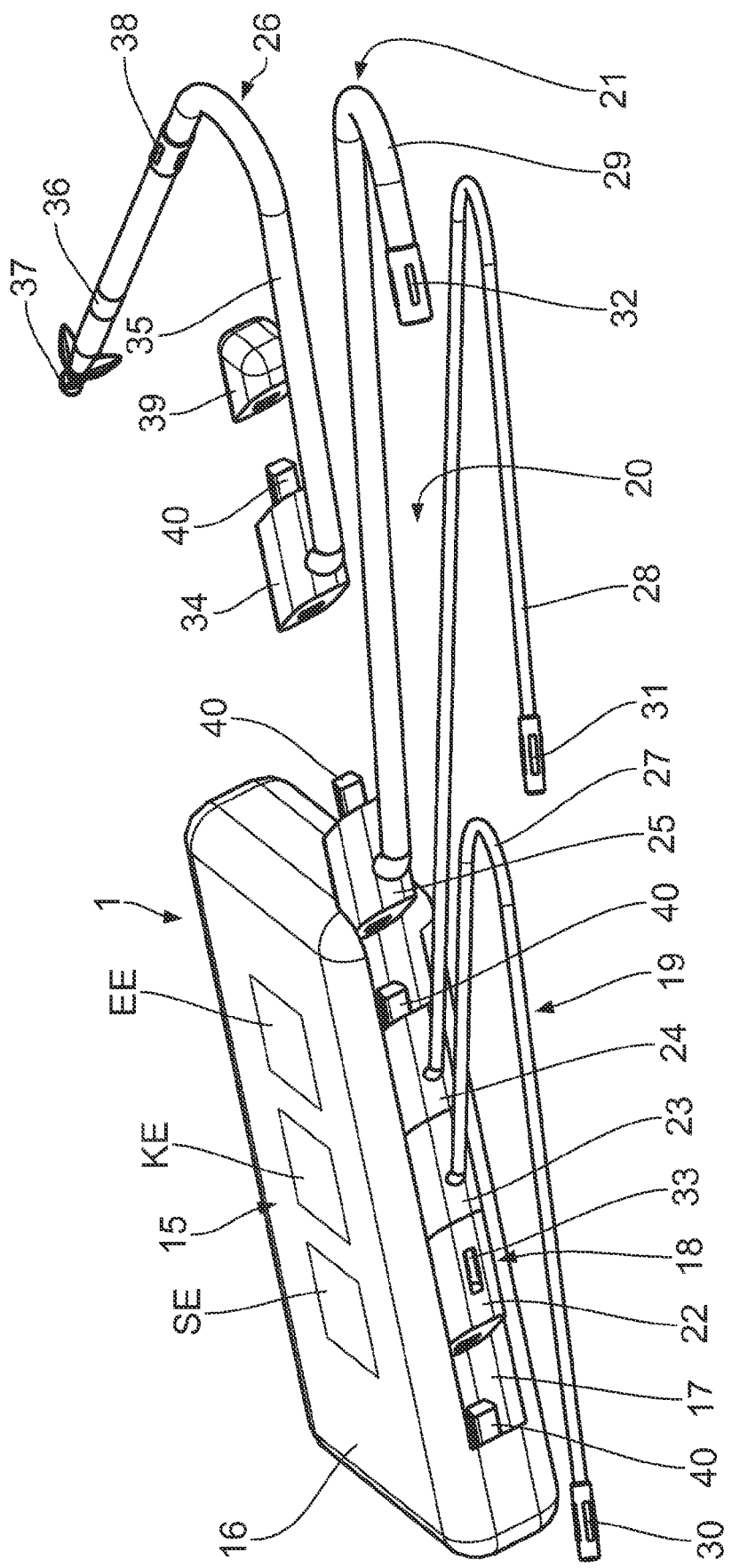
FIG. 2 shows a perspective representation of such an implantable device with different implant modules.

An implementation of the module system represented diagrammatically in FIG. 1 can be explained with reference to FIG. 2. Thus a basic device component 15 represents the "backbone" of medical implantable device 1. A central control unit SE, a communication unit KE, and a power supply unit EE are permanently installed in this basic device component 15 as multi-function basic elements. In the exemplary embodiment shown diagnostic and therapeutic modules are now provided for coupling to basic device component 15. For this purpose basic device component 15 has, on the long narrow side of its housing 16, a coupling bar 17, which is formed by a corresponding housing groove into which can be inserted mechanically the different modules shown, namely measuring modules 18, 19, 20, 21, for example, with their respective module heads 22 to 25. Module heads 22 to 24 are shown in FIG. 2 in a position in which they have not yet been slid through as far as coupling bar 17 (on the left in FIG. 2). Measuring module 21 and therapy module 26 are shown in the condition where they are not yet docked.

All measuring modules 18 to 21 have measuring cables 27 to 29 running from module heads 22 to 25, on the free ends of which cables measuring sensors 30 to 32, e.g. for pressure, pH value or the like, are in turn arranged. In measuring module 18 temperature sensor 33 is inserted directly into module head 22.

Therapy module 26 has on its module head 34 a catheter 35 which supports stimulation electrodes 36, 37 at it free end. Furthermore, a measuring sensor 38, e.g. for pressure or temperature, is provided on catheter 35.

To complete the implantable device shown in FIG. 2 a sealing cap 39 is also provided, which is placed on the last module head 34 and serves to seal the bus system 13 guided through module heads 22 to 25, 34. Bus system 13 is constructed so that it extends via basic device component 15 and modules 18 to 21, 26 through suitable plug-in connections 40 between module heads 22 to 25, 34 to basic device component 15.

Figure 3:
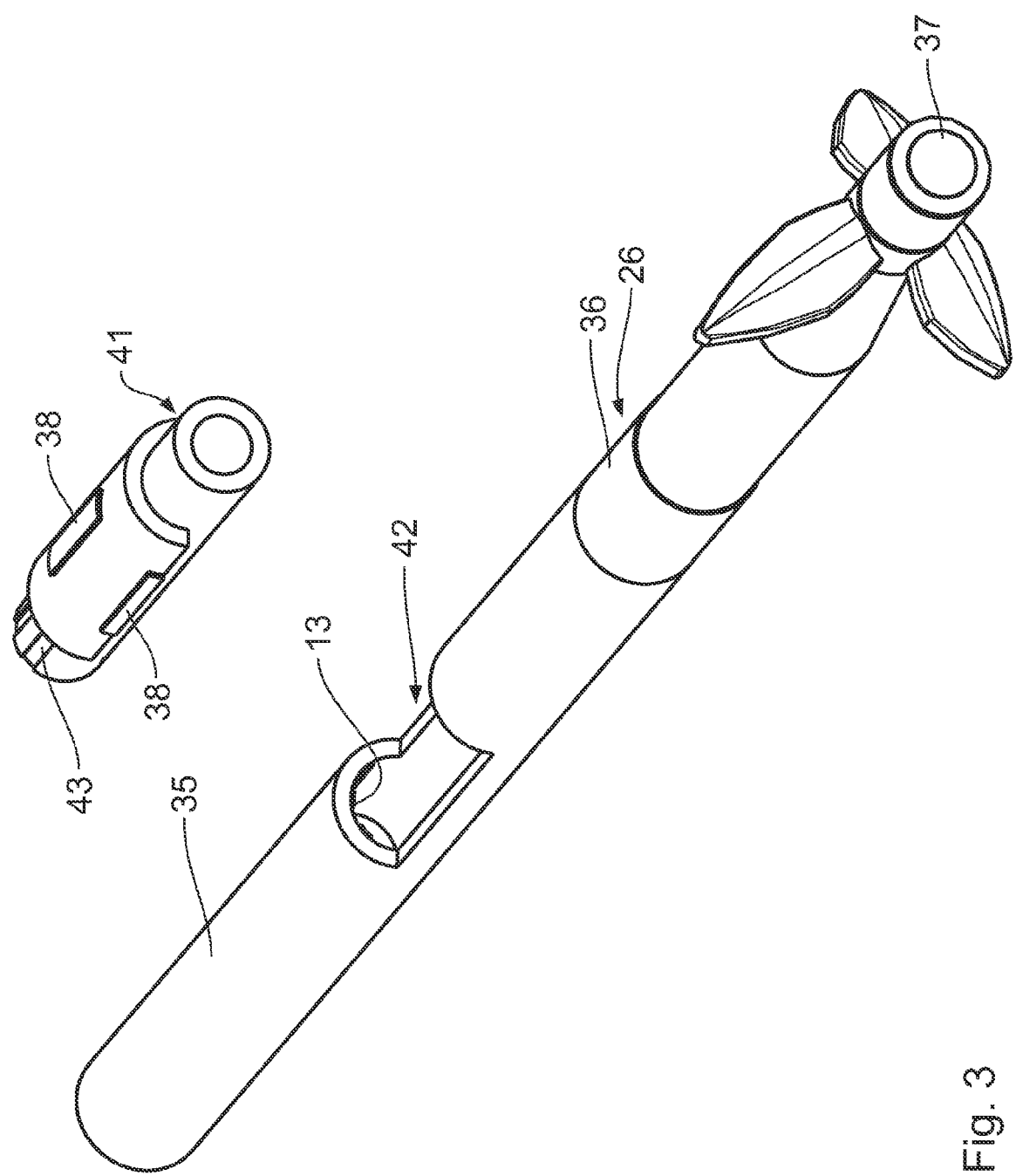
FIG. 3 shows a sectional perspective representation of an implant module.

FIG. 3 shows in sections catheter 35 in the region of the distal end. It can be seen from this that measuring sensor 38 may itself be designed in turn as a replaceable sub-module 41. As already mentioned, this supports a measuring sensor, e.g. for pressure or temperature. The functionality of sub-module 41 is therefore of a diagnostic nature, whilst stimulation electrodes 36, 37 on therapy module 26 produce a therapeutic effect.

Sub-module 41 may be inserted in a corresponding recess 42 in catheter 35. Here the coupling to the control module (not shown here) is made by a plug-in connection 43 to bus system 13.

It should be added that modules 18 to 21, 26, 41 are able to communicate uni-, bi- or multi-directionally with each other and with the central control module via bus system 13. For control, a master-and-slave control system, with reference to the hierarchical arrangement of modules 18 to 21, 26, can be implemented.

What is claimed is:

1. An active medical implantable device with at least two functions that include any combination of diagnostic and/or therapeutic functions comprising:
   a basic device component having
      a central control unit and
      a mechanical coupling bar configured as a groove in a side of the active medical implantable device and
      a bus system coupled with said central control unit and
      a first plug-in connection mechanically coupled with said coupling bar wherein said plug-in connection comprises said bus system;
   active implant modules, a separate one for each of the at least two functions, mechanically coupled to the basic device component via said coupling bar and direct mechanically coupled to one another on two opposing sides of said active implant modules and electrically coupled to one another via the bus system;
   a sealing cap mechanically coupled to a furthest active implant module away from said first plug-in connection wherein said sealing cap is configured to electrically terminate said bus system;
   said active implant modules configured to be coupled with or removed from said basic device component without removal of said basic device component from a body in which said basic device component is implanted after said sealing cap is removed from said furthest active implant module away from said first plug-in connection an particular one of active implant modules is mechanically coupled with or removed from said coupling bar and mechanically and electrically coupled with or removed from at least one of said active implant modules and wherein said sealing cap is again coupled with said furthest active implant module away from said first plug-in connection;
   at least two further plug-in connections, each attached to said respective active implant modules wherein said at least two further plug-in connections are configured to extend said bus system;
   wherein the active implant modules are configured to communicate unidirectionally, bidirectionally or multidirectionally with the central control unit via the bus system and are controlled by central control unit, and wherein the active implant modules are configured to communicate with one another unidirectionally, bidirectionally or multidirectionally via the bus system.

2. The implantable device according to claim 1, wherein the central control unit implements a master and slave control with regard to a hierarchical order of the active implant modules.

3. The implantable device according to claim 1, wherein said basic device component is configured to receive additional multi-functional basic elements for the active implant modules.

4. The implantable device according to claim 3, wherein said additional multi-functional basic elements of said basic device component comprise a communication unit and/or a power supply unit for said active implant modules.

5. The implantable device according to claim 1, wherein an implant module selected from said active implant modules can be fitted with at least one replaceable sub-module, with functionality that deviates from said implant module.

6. The implantable device according to claim 1, wherein one of said active implant modules, is configured as a master device which controls further coupled implant modules.

* * * * *